(12) United States Patent
Heath

(10) Patent No.: US 6,290,721 B1
(45) Date of Patent: *Sep. 18, 2001

(54) TUBULAR MEDICAL ENDOPROSTHESES

(75) Inventor: Kevin R. Heath, Providence, RI (US)

(73) Assignee: Boston Scientific Corporation, Maple Grove, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/955,268

(22) Filed: Oct. 21, 1997

Related U.S. Application Data

(63) Continuation of application No. 08/478,007, filed on Jun. 7, 1995, now abandoned, which is a continuation of application No. 08/282,776, filed on Jul. 29, 1994, now abandoned, which is a continuation of application No. 07/910,631, filed on Jul. 8, 1992, now abandoned, which is a continuation-in-part of application No. 07/861,253, filed on Mar. 31, 1992, now abandoned.

(51) Int. Cl.⁷ ....................................................... A61F 2/06
(52) U.S. Cl. ......................................... 623/1.15; 623/1.18
(58) Field of Search ....................... 623/1, 12, 1.15–1.22; 606/195, 198

(56) References Cited

U.S. PATENT DOCUMENTS

| | | |
|---|---|---|
| 2,524,661 | 10/1950 | Harder et al. . |
| 3,196,876 | 7/1965 | Miller . |
| 3,335,443 | 8/1967 | Parisi et al. . |
| 3,466,166 | 9/1969 | Levinstein et al. . |
| 3,528,410 | 9/1970 | Banko . |
| 3,558,066 | 1/1971 | Alliger . |
| 3,562,024 | 2/1971 | Smith et al. . |
| 3,584,327 | 6/1971 | Murry . |
| 3,589,363 | 6/1971 | Banko et al. . |
| 3,605,750 | 9/1971 | Sheridan . |

(List continued on next page.)

FOREIGN PATENT DOCUMENTS

| | | |
|---|---|---|
| 1324553 | 11/1993 | (CA) . |
| 33 29 176 C1 | 11/1984 | (DE) . |
| 40 22 956 A1 | 2/1992 | (DE) . |

(List continued on next page.)

OTHER PUBLICATIONS

DFT–Drawn Filled Tubing Publication; Brochure Published in 1988.*
Assefpour–Dezfuly et al., Journal of Materials Science, Nov. 1983, pp. 2815–2936.
Klinger and Kurisky, "MP35N alloy—the ultimate wire material", *Wire Journal*, 1980.
Metals Handbook, Tenth Edition, vol. 1, ASM International, Materials Park, OH 1990.
Metals Handbook, Tenth Edition, vol. 2, ASM International, Materials Park, OH.

(List continued on next page.)

Primary Examiner—Corrine McDermott
Assistant Examiner—Hieu Phan
(74) Attorney, Agent, or Firm—Fish & Richardson P.C.

(57) ABSTRACT

A tubular prosthesis device for use within the body. The device includes, a metal filament material formed of metal outer member having an exposed outer surface and a core within the extended outer member formed of a different metal than the outer member. The core is secured within and substantially enclosed by the outer member. The device can be reduced to a small size for introduction into the body lumen and expandable to a sufficiently large size to engage the wall of the body lumen. Stents formed of composite wires are shown.

55 Claims, 5 Drawing Sheets

U.S. PATENT DOCUMENTS

| Number | Date | Name | Ref |
|---|---|---|---|
| 3,618,594 | 11/1971 | Banko . | |
| 3,618,614 | 11/1971 | Flynn . | |
| 3,749,086 | 7/1973 | Kline et al. . | |
| 3,805,787 | 4/1974 | Banko . | |
| 3,823,717 | 7/1974 | Pohlman et al. . | |
| 3,830,240 | 8/1974 | Antonevich et al. . | |
| 3,861,391 | 1/1975 | Antonevich et al. . | |
| 3,896,811 | 7/1975 | Storz . | |
| 3,930,173 | 12/1975 | Banko . | |
| 3,941,122 | 3/1976 | Jones . | |
| 3,942,519 | 3/1976 | Shock . | |
| 3,956,826 | 5/1976 | Perdreaux, Jr. . | |
| 4,023,557 | 5/1977 | Thorne et al. . | |
| 4,041,931 | 8/1977 | Elliott et al. . | |
| 4,178,935 | 12/1979 | Gekhman et al. . | |
| 4,188,952 | 2/1980 | Loshilov et al. . | |
| 4,202,349 | 5/1980 | Jones . | |
| 4,281,419 | 8/1981 | Treace . | |
| 4,295,464 | 10/1981 | Shihata . | |
| 4,345,602 | 8/1982 | Yoshimura et al. . | |
| 4,351,326 | 9/1982 | Kosonen . | |
| 4,370,131 | 1/1983 | Banko . | |
| 4,380,574 | 4/1983 | Gessinger et al. . | |
| 4,406,284 | 9/1983 | Banko . | |
| 4,417,578 | 11/1983 | Banko . | |
| 4,425,115 | 1/1984 | Wuchinich . | |
| 4,425,908 | 1/1984 | Simon . | |
| 4,464,176 | 8/1984 | Wijayarathna . | |
| 4,465,481 | 8/1984 | Blake . | |
| 4,474,180 | 10/1984 | Angulo . | |
| 4,486,680 | 12/1984 | Bonnet et al. . | |
| 4,504,268 | 3/1985 | Herlitze . | |
| 4,517,793 | 5/1985 | Carus . | |
| 4,518,444 | 5/1985 | Albrecht et al. . | |
| 4,535,759 | 8/1985 | Polk et al. . | |
| 4,553,564 | 11/1985 | Maass et al. . | |
| 4,561,438 | 12/1985 | Bonnet et al. . | |
| 4,572,184 | 2/1986 | Stohl et al. . | |
| 4,577,637 | 3/1986 | Mueller, Jr. . | |
| 4,580,568 | 4/1986 | Gianturco . | |
| 4,600,446 | 7/1986 | Torisaka et al. . | |
| 4,602,633 | 7/1986 | Goodfriend et al. . | |
| 4,615,331 | 10/1986 | Kramann . | |
| 4,654,092 | 3/1987 | Melton . | |
| 4,655,771 | 4/1987 | Wallsten . | |
| 4,657,024 | 4/1987 | Coneys . | |
| 4,681,110 | 7/1987 | Wiktor | 128/343 |
| 4,692,139 | 9/1987 | Stiles . | |
| 4,697,595 | 10/1987 | Breyer et al. . | |
| 4,698,058 | 10/1987 | Greenfeld et al. . | |
| 4,706,681 | 11/1987 | Breyer et al. . | |
| 4,719,916 | 1/1988 | Ravo . | |
| 4,724,846 | 2/1988 | Evans, III . | |
| 4,731,084 | 3/1988 | Dunn et al. . | |
| 4,732,152 | 3/1988 | Wallsten et al. . | |
| 4,733,665 | 3/1988 | Palmaz . | |
| 4,748,971 | 6/1988 | Borodulin et al. . | |
| 4,748,986 | 6/1988 | Morrison et al. . | |
| 4,750,488 | 6/1988 | Wuchinich et al. . | |
| 4,750,902 | 6/1988 | Wuchinich et al. . | |
| 4,751,916 | 6/1988 | Bory . | |
| 4,760,849 | 8/1988 | Kropf . | |
| 4,768,507 | 9/1988 | Fischell . | |
| 4,770,664 | 9/1988 | Gogolewski . | |
| 4,771,773 | 9/1988 | Kropf . | |
| 4,793,348 | 12/1988 | Palmaz . | |
| 4,796,637 | 1/1989 | Mascuch et al. . | |
| 4,800,890 | 1/1989 | Cramer . | |
| 4,808,246 | 2/1989 | Albrecht et al. . | |
| 4,816,018 | 3/1989 | Parisi . | |
| 4,817,600 | 4/1989 | Herms et al. . | |
| 4,819,618 | 4/1989 | Liprie . | |
| 4,823,793 | 4/1989 | Angulo et al. . | |
| 4,830,003 | 5/1989 | Wolff et al. | 128/343 |
| 4,830,023 | 5/1989 | de Toledo et al. . | |
| 4,830,262 | 5/1989 | Ishibe . | |
| 4,834,747 | 5/1989 | Gogolewski . | |
| 4,842,590 | 6/1989 | Tanabe et al. . | |
| 4,846,186 | 7/1989 | Box et al. . | |
| 4,848,343 | 7/1989 | Wallsten . | |
| 4,848,348 | 7/1989 | Craighead . | |
| 4,850,999 | 7/1989 | Planck . | |
| 4,856,516 | 8/1989 | Hillstead . | |
| 4,867,173 | 9/1989 | Leoni . | |
| 4,870,953 | 10/1989 | DonMicheal et al. . | |
| 4,875,480 | 10/1989 | Imbert . | |
| 4,883,486 | 11/1989 | Kapadia et al. . | |
| 4,884,579 | 12/1989 | Engelson . | |
| 4,886,062 | 12/1989 | Wiktor . | |
| 4,899,733 | 2/1990 | DeCastro et al. . | |
| 4,906,241 | 3/1990 | Noddin . | |
| 4,907,572 | 3/1990 | Borodulin et al. . | |
| 4,920,954 | 5/1990 | Alliger et al. . | |
| 4,922,905 | * 5/1990 | Strecker | 606/195 |
| 4,922,924 | 5/1990 | Gambale et al. . | |
| 4,925,445 | 5/1990 | Sakamoto et al. . | |
| 4,932,419 | 6/1990 | de Toledo . | |
| 4,934,380 | 6/1990 | de Toledo . | |
| 4,936,845 | 6/1990 | Stevens . | |
| 4,950,227 | 8/1990 | Savin et al. . | |
| 4,953,553 | 9/1990 | Tremulis | 128/637 |
| 4,954,126 | 9/1990 | Wallsten . | |
| 4,957,110 | 9/1990 | Vogel et al. . | |
| 4,964,409 | 10/1990 | Tremulis . | |
| 4,969,891 | 11/1990 | Gewertz . | |
| 4,971,490 | 11/1990 | Hawkins | 128/772 |
| 4,980,964 | 1/1991 | Boeke . | |
| 4,984,581 | 1/1991 | Stice . | |
| 4,989,608 | 2/1991 | Ratner . | |
| 4,990,151 | 2/1991 | Wallsten . | |
| 4,995,878 | 2/1991 | Rai . | |
| 5,001,825 | 3/1991 | Halpern . | |
| 5,003,987 | 4/1991 | Grinwald . | |
| 5,003,989 | 4/1991 | Taylor . | |
| 5,012,797 | 5/1991 | Liang et al. . | |
| 5,015,183 | 5/1991 | Fenick . | |
| 5,015,253 | 5/1991 | MacGregor . | |
| 5,019,085 | 5/1991 | Hillstead . | |
| 5,019,090 | 5/1991 | Pinchuk . | |
| 5,024,232 | 6/1991 | Smid et al. . | |
| 5,024,617 | 6/1991 | Karpiel . | |
| 5,025,799 | 6/1991 | Wilson . | |
| 5,026,377 | 6/1991 | Burton et al. . | |
| 5,040,280 | 8/1991 | Takada . | |
| 5,040,283 | 8/1991 | Pelgrom . | |
| 5,047,050 | 9/1991 | Arpesani . | |
| 5,052,407 | 10/1991 | Hauser et al. . | |
| 5,059,166 | 10/1991 | Fischell et al. . | |
| 5,061,275 | 10/1991 | Wallsten et al. . | |
| 5,064,428 | 11/1991 | Cape et al. . | |
| 5,064,435 | 11/1991 | Porter . | |
| 5,069,217 | 12/1991 | Fleischacker, Jr. . | |
| 5,069,226 | 12/1991 | Yamauchi et al. | 128/772 |
| 5,071,407 | 12/1991 | Termin et al. . | |
| 5,092,877 | 3/1992 | Pinchuk . | |
| 5,095,915 | 3/1992 | Engelson . | |
| 5,104,404 | 4/1992 | Wolff . | |
| 5,109,830 | 5/1992 | Cho . | |
| 5,111,829 | 5/1992 | de Toledo . | |
| 5,129,890 | 7/1992 | Bates et al. . | |
| 5,139,480 | 8/1992 | Hickle et al. . | |

| | | |
|---|---|---|
| 5,147,317 | 9/1992 | Shank et al. . |
| 5,147,385 | 9/1992 | Beck et al. . |
| 5,152,777 | 10/1992 | Goldberg . |
| 5,163,433 | 11/1992 | Kagawa et al. . |
| 5,163,952 * | 11/1992 | Froix ........................................ 623/1 |
| 5,171,233 | 12/1992 | Amplatz et al. . |
| 5,171,262 | 12/1992 | MacGregor . |
| 5,176,617 | 1/1993 | Fischell et al. . |
| 5,197,978 * | 3/1993 | Hess ......................................... 623/1 |
| 5,201,901 * | 4/1993 | Harada et al. ........................... 623/1 |
| 5,207,706 | 5/1993 | Menaker . |
| 5,213,111 | 5/1993 | Cook et al. . |
| 5,217,483 | 6/1993 | Tower . |
| 5,256,158 | 10/1993 | Tolkoff et al. . |
| 5,256,764 | 10/1993 | Tang et al. . |
| 5,276,455 | 1/1994 | Fitzsimmons et al. . |
| 5,304,140 | 4/1994 | Kugo et al. . |
| 5,320,100 | 6/1994 | Herweck et al. . |
| 5,334,201 | 8/1994 | Cowan . |
| 5,354,309 | 10/1994 | Schnepp-Pesch et al. . |
| 5,360,442 | 11/1994 | Dahl et al. . |
| 5,366,504 * | 11/1994 | Andersen et al. ....................... 623/1 |
| 5,368,661 | 11/1994 | Nakamura et al. . |
| 5,374,261 | 12/1994 | Yoon . |
| 5,382,259 | 1/1995 | Phelps et al. . |
| 5,389,106 | 2/1995 | Tower . |
| 5,474,563 | 12/1995 | Myler et al. . |
| 5,476,508 | 12/1995 | Amstrup . |
| 5,489,227 | 2/1996 | Tolkoff et al. . |
| 5,496,330 | 3/1996 | Bates . |
| 5,498,236 | 3/1996 | Dubrul et al. . |
| 5,514,154 | 5/1996 | Lau et al. . |
| 5,556,413 | 9/1996 | Lam . |
| 5,609,629 | 3/1997 | Fearnot et al. . |
| 5,628,787 | 5/1997 | Mayer ..................................... 623/1 |
| 5,630,840 | 5/1997 | Mayer . |
| 5,658,296 | 8/1997 | Bates . |
| 5,690,670 * | 11/1997 | Davidson ................................ 623/1 |
| 5,725,549 | 3/1998 | Lam . |
| 5,725,570 * | 3/1998 | Heath ...................................... 623/1 |
| 5,733,326 | 3/1998 | Tomonto et al. . |
| 5,843,163 | 12/1998 | Wall . |
| 5,849,037 * | 12/1998 | Frid ......................................... 623/1 |
| 5,858,556 | 1/1999 | Eckert et al. . |
| 5,879,382 * | 4/1999 | Boneau ................................... 623/1 |
| 5,891,191 * | 4/1999 | Stinson ................................... 623/1 |
| 5,902,332 * | 5/1999 | Schatz .................................... 623/1 |

FOREIGN PATENT DOCUMENTS

| | | |
|---|---|---|
| 92 06 170 | 8/1992 | (DE) ............................ A61B/6/00 |
| 0 067 929 | 12/1982 | (EP) . |
| 0 121 447 | 10/1984 | (EP) ............................. A61F/1/00 |
| 0 221 570 | 5/1987 | (EP) . |
| 0 405 429 A2 | 1/1991 | (EP) . |
| 0 405 823 A2 | 1/1991 | (EP) . |
| 0 433 011 | 6/1991 | (EP) ............................ A61F/2/06 |
| 0 433 011 A1 | 6/1991 | (EP) . |
| 0 435 518 A1 | 7/1991 | (EP) . |
| 0 042 703 A1 | 12/1991 | (EP) . |
| 0 481 365 A1 | 4/1992 | (EP) . |
| 0 547 739 A1 | 6/1993 | (EP) . |
| 0 556 940 A1 | 8/1993 | (EP) . |
| 0 593 136 A1 | 4/1994 | (EP) . |
| 2 479 685 | 3/1981 | (FR) . |
| 1 205 743 | 9/1970 | (GB) . |
| 2 195 257 A | 4/1988 | (GB) . |
| 53-19958 | 2/1978 | (JP) . |
| 1-259541 | 10/1989 | (JP) . |
| WO 88/01924 | 3/1988 | (WO) . |
| WO 90/01300 | 2/1990 | (WO) .......................... A61B/17/32 |
| WO 91/04716 | 4/1991 | (WO) ............................ A61F/2/02 |
| WO91/19528 | 12/1991 | (WO) . |
| WO 92/11815 | 7/1992 | (WO) ............................ A61B/17/22 |
| WO 92/13483 | 8/1992 | (WO) . |
| WO 92/19310 | 12/1992 | (WO) ........................... A61M/29/00 |
| WO 92/21399 | 12/1992 | (WO) . |
| WO 93/19803 | 10/1993 | (WO) . |
| WO 93/19804 | 10/1993 | (WO) . |
| WO 94/16646 | 8/1994 | (WO) . |
| WO 94/24961 | 11/1994 | (WO) . |
| 97/04895 | 2/1997 | (WO) . |
| WO 97/04895 | 2/1997 | (WO) . |

OTHER PUBLICATIONS

Schneider, PCT/US93/11262 Search Report, Nov. 1993.

Schneider, PCT/IB95/00253 Search Report, Oct. 1995.

Sigwart et al., *The New England Journal of Medicine*, vol. 316, Mar. 19, 1987.

Alliger, "Ultrasonic Disruption", Am. Lab. (a journal), vol. 7, No. 10, 1975, pp. 75–76, 78, 80–82, 84, and 85.

Alliger et al., "Tumoricidal Effect of a New Ultrasonic Needle", Federation Proceedings–Abstracts, vol. 44, No. 4, Mar. 5, 1985, p. 1145.

Ariani et al., "Dissolution of Peripheral Arterial Thrombi by Ultrasound", Circulation (American Heart Association), vol. 84, No. 4, Oct. 1991, pp. 1680–1688.

Chae et al., "Ultrasonic Dissolution of Human Thrombi", Journal of the American College of Cardiology, vol. 15, No. 7, Jun. 1990, p. 65A.

Chaussy et al., "Transurethral Ultrasonic Ureterolithotripsy Using a Solid–Wire Probe", Urology, vol. XXIX, No. 5, May 1987, pp. 531–532.

Chaussy et al., "Transurethral Ultrasonic Uretero–lithotripsy: A New Technique", The Journal of Urology, vol. 137, No. 4, Part 2, Apr. 1987, p. 159A.

Demer et al., "High Intensity Ultrasound Increases Distensibility of Calcific Atherosclerotic Arteries", Journal of the American College of Cardiology, vol. 18, No. 5, Nov. 1, 1991, pp. 1259–1262.

Ernst et al., "Ability of High–Intensity Ultrasound to Ablate Human Atherosclerotic Plaques and Minimize Debris Size", The American Journal of Cardiology, vol. 68, No. 2, Jul. 15, 1991, pp. 242–246.

Freeman et al., "Ultrasonic Angioplasty Using a New Flexible Wire System", Journal of the American College of Cardiology, vol. 13, No. 1, Jan. 1989, p. 4A.

Freeman et al., "Ultrasonic Energy Produces Endothelium–Dependent Vasomotor Relaxation In Vitro", Clinical Research–Official Publication of The Amer. Federation for Clinical Research, vol. 36, No. 5, Sep. 5, 1988, p. 786A.

Goodfriend, "Ultrasonic Ureterolithotripsy Employed in a Flexible Ureteroscope", The Journal of Urology, vol. 139, No. 4, Part 2, Apr. 1988, p. 282A.

Goodfriend, "Ultrasonic and Electrohydraulic Lithotripsy of Ureteral Calculi", Urology, vol. XXIII, No. 1, Jan. 1984, pp. 5–8.

Goodfriend, "Transvesical Intussusception Ureterectomy", vol. XXI, No. 4, Apr. 1983, pp. 414–415.

Goodfriend, "Disintegration of Ureteral Calculi by Ultrasound", Urology, vol. 1, No. 3, Mar. 1973, pp. 260–263.

Hong et al., "Ultrasonic clot disruption: An in vitro study", American Heart Journal, vol. 20, No. 2, Aug. 1990, pp. 418–422.

Hunter et al., "Transurethral Ultrasonic Uretero–lithotripsy", The Journal of Urology, vol. 135, No. 4, Part 2, Apr. 1986, p. 299A.

Marco et al., "Intracoronary Ultra Sound Imaging: Preliminary Clinical Results", European Heart Journal–Journal of the European Society of Cardiology–Abstract Supplement (Academic Press), Aug. 1990, p. 190.

Monteverde et al., "Ultrasound Arterial Recanalization in Acute Myocardial Infarction", Supplement to Circulation (American Heart Association), vol. 82, No. 4, Oct. 1990, p. III–622.

Monteverde et al., "Percutaneous Transluminal Ultrasonic Angioplasty in Totally Occluded Peripheral Arteries: Immediate and Intermediate Clinical Results", Supplement to Circulation (American Heart Association), vol. 82, No. 4, Oct. 1990, p. 111–678.

Rosenschein et al., "Clinical Experience with Ultrasonic Angioplasty of Totally Occluded Peripheral Arteries", Journal of the American College of Cardiology, vol. 15, No. 1, Jan. 1990, p. 104A.

Siegel et al., "In Vivo Ultrasound Arterial Recanalization of Atherosclerotic Total Occlusions", Journal of the American College of Cardiology, vol. 15, No. 2, Feb. 1990, pp. 345–351.

Siegel et al., "Percutaneous Ultrasonic Angioplasty: Initial Clinical Experience", The Lancet, vol. II, No. 8666, Sep. 30, 1989, pp. 772–774.

Siegel et al., "Ultrasonic Plaque Ablation–A New Method for Recanalization of Partially or Totally Occluded Arteries", Circulation, vol. 78, No. 6, Dec. 1988, pp. 1443–1448.

Katzen Infusion Wire, Meditech, Apr. 1991.

"Standard Test Methods for Radiopacity of Plastics for Medical Use," ASTM Designation F 640–79, pp. 1074–1078, 1980.

* cited by examiner

TUBULAR MEDICAL ENDOPROSTHESES

CROSS-REFERENCE TO RELATED APPLICATION

This is a continuation of application Ser. No. 08/478,007 filed on Jun. 7, 1995, now abandoned, which is a continuation of application Ser. No. 08/282,776 now abandoned, filed Jul. 29, 1994, which is a continuation of application Ser. No. 07/910,631, filed Jul. 8, 1992 now abandoned, which is a continuation-in-part of application Ser. No. 07/861,253, filed Mar. 31, 1992 now abandoned.

FIELD OF THE INVENTION

This invention relates to tubular endoprostheses to be used inside the body.

BACKGROUND OF THE INVENTION

Tubular endoprostheses such as medical stents are placed within the body to perform a function such as maintaining a body lumen open, for example, a passageway occluded by a tumor or a blood vessel restricted by plaque. Tubular endoprostheses in the form of grafts are used to substitute for or reinforce a lumen, such as the aorta or other blood vessels which have been weakened, e.g., by an aneurysm.

Typically, these endoprostheses are delivered inside the body by a catheter that supports the device in a compacted or otherwise reduced-size form as it is transported to the desired site. The size is particularly small when a percutaneous insertion technique is employed. Upon reaching the site, the endoprosthesis is expanded so that it engages the walls of the lumen.

The expansion mechanism may involve forcing the endoprosthesis to expand radially outwardly, for example, by inflation of a balloon carried by the catheter, to plastically deform and fix the device at a predetermined expanded position in contact with the lumen wall. The expanding means, the balloon, can then be deflated and the catheter removed.

In another technique, the endoprosthesis is formed of a highly elastic material that can be reversibly compacted and expanded. During introduction into the body, the endoprosthesis is restrained in the compacted condition and upon reaching the desired site for implantation, the restraint is removed, enabling the device to self-expand by its own internal elastic restoring force.

In many cases, X-ray fluoroscopy is used to view an endoprosthesis within the body cavity to monitor placement and operation. The device may also be viewed by X-ray film after placement for medical follow-up evaluation. To date, the requirement for radiopacity has limited the construction of devices to certain materials which in turn has limited the features attainable for particular applications and the available insertion techniques.

SUMMARY OF THE INVENTION

In the invention, metal such as in the form of wire or filament or the like is used for constructing tubular medical endoprosthesis such as stents. Desirable attributes of these wires vary with the stent application, but include properties such as stiffness, tensile strength, elasticity, radiopacity, weldability, flexural life, conductivity, etc. These properties are hard to find in conventional wires. According to the invention, desired properties are achieved by creating a multiple metal coaxial construction. For example, it may be very desirable to have high radiopacity along with elasticity and strength. This is accomplished by combining a radiopaque metal with an elastic metal. Although it is possible to put either metal on the inside or outside, it is preferable to put the dense radiopaque material (e.g., tantalum) on the inside (core) since dense materials are generally less elastic and the elastic material (e.g., titanium or nickel-titanium alloy) on the outside (clad). The clad or "skin" of the wire will undergo more deformation in bending than the core, so the elastic component is best positioned at the skin.

Thus, an aspect of the invention is a metal stent device with at least a portion to be used within the body having properties that can be tailored to a particular application. The portion within the body is formed of preferably two or more dissimilar metals joined together to form a unitary member. Typically, each metal contributes a desirable property to the device which is not substantially impaired by the presence of the other metal. In particularly preferred devices, one metal provides enhanced radiopacity. In these embodiments, the stent is comprised of a metal outer member having a predetermined density and an exposed outer surface and a core including a metal having a density greater than the outer member to enhance radiopacity. The core is secured within and substantially enclosed by the outer member. Preferably, the stent is configured such that the mechanical properties, for example, the elastic properties, of the metal forming the outer member are affected by the core to a desired degree so that the stent has a desired overall performance suitable for its intended use. Preferably, the mechanical properties of the outer member dominate the properties of the stent yet the radiopacity of the member is substantially enhanced by the denser core. The invention also allows increased radiopacity of the stent without adversely affecting and in some cases improving other important properties such as the biocompatibility, small size or other performance characteristics. These performance advantages can be realized by proper selection of the material of the outer member and core, their relative size, and geometrical configuration. The particular performance characteristics to be achieved are dictated by the stent application.

The term "metal" as used herein includes electropositive chemical elements characterized by ductility, malleability, luster, and conductivity of heat and electricity, which can replace the hydrogen of an acid and forms bases with the hydroxyl radical and including mixtures including these elements and alloys. Many examples are given below.

An aspect of the invention features a tubular prosthesis device for use within the body. Forming the tubular endoprosthesis is a metal filament material comprised of a metal outer member of extended length having an exposed outer surface and a core within the extended outer member formed of a different metal than the outer member. The core is secured within and substantially enclosed by the outer member. The device is capable of reduction to a small size for introduction into the body lumen and expandable to a sufficiently large size to engage the wall of the body lumen.

In some preferred embodiments, the outer member and core are such that the endoprosthesis is elastic and capable of radial reduction in size without plastic deformation to the small size for introduction to the body and self-expandable by an internal elastic self-restoring force to the large size for engaging the wall of the lumen.

In other embodiments, the outer member and core are such that the endoprosthesis is plastically deformable; it is formed of small size for introduction into the body and expandable by plastic deformation to the large size for engaging the wall of the lumen.

Various embodiments of the invention may also include one or more of the following features. The device is formed into the tubular shape by knitting of the wire or filament into loosely interlocked loops of the filament. The metal of the core has a density greater than the metal of the outer member of the device. The cross sectional dimension of the filament is about 0.015 inch or less. The cross-sectional dimension of the filament is about 0.006 to about 0.0045 inch and the core has a cross-sectional dimension of about 0.0014 to about 0.00195 inch. The core has a density of about 9.9 g/cc or greater. The core is selected form the group consisting of tungsten, tantalum, rhenium, iridium, silver, gold, bismuth and platinum. The outer member is selected from superelastic alloys and precursors of superelastic alloys and stainless steel. The outer member is nitinol. The core is tantalum.

Another, particular aspect of the invention features a self-expanding tubular prosthesis device for use within the body formed of loosely interlocked knitted loops of a metal filament material. The filament is formed of an elastic metal capable of deflection without plastic deformation to produce a self-restoring force. The filament material is formed of an elastic metal outer member of extended length having high elasticity and an exposed outer surface, and a core of a different metal than the outer member, which core is secured within and substantially enclosed by the outer member. The device is capable of reduction to a small size for introduction into the body lumen and expandable by the internal restoring force to a sufficiently large size to engage the wall of the body lumen.

Various embodiments of this aspect as well as other aspects may include the features already mentioned as well as one or more of the following features. The core is about 25% or more of the cross-sectional dimension. The core is between about 1 and 40%, e.g. about 28% or less, preferably 33% of the cross-sectional dimension. The core has a modulus of elasticity of about 500 GPa or less, such as about 200 GPa or less.

In another aspect the invention features a medical stent device capable of placement or manipulation in the body by means external of the body under guidance of a fluoroscope. The device is at least in part an elongated filament-form metal member adapted to be subjected to elastic deformation to enable the device to be forced into a characteristic deformed configuration during a stage of use and to elastically self-recover from the deformation when deformation forces are relieved. The filament-form metal member includes a core of a first metal of a first selected thickness and an intimately surrounding sheath of a second selected metal of a second thickness. The first metal is a high density metal that demonstrates characteristic relatively high radiopacity and the second metal is a lower density metal having substantially more elasticity than the first metal. The combined effect of the selected thicknesses of the first and second metals in the filament-form member serves to enhance the radio-opacity of the filament-form member to provide improved fluoroscopic or x-ray visualization of the filament-form member in the body while imparting sufficient elasticity to enable the filament-form member to elastically self-recover from its characteristic deformed configuration.

In another aspect, the invention features a tubular endoprosthesis formed of a metal member. The metal member has a cross-sectional thickness of about 0.015 inch or less, more preferably 0.0075 inch or less, and is composed of at least two different metals, including an exposed outer metal having selected mechanical properties and an inner metal encompassed within the outer metal, the inner metal having a relatively high density compared to the outer metal for enhancing the radiopacity of the endoprosthesis.

In various embodiments of any of the aspects of the invention the filament is formed by draw-forming techniques employing a large starting member which has a core of metal of different properties than a surrounding metal shell.

The invention also includes methods for the use and construction of the endoprostheses described.

Still other aspects of the invention will be understood from the following description and from the claims.

DESCRIPTION OF THE PREFERRED EMBODIMENT(S)

We first briefly describe the drawings.

DRAWINGS

FIG. 1 is a perspective view of a stent according to the invention, while

FIG. 2 is a highly enlarged schematic cross-sectional view of the stent filament in FIG. 1a across the lines 22; while

DESCRIPTION

Figure 1:
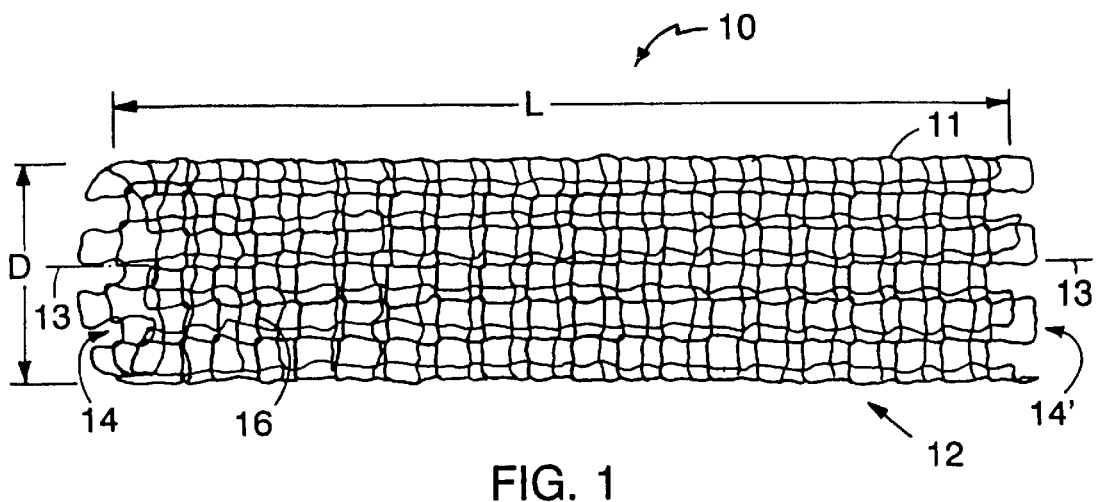
Figure 1A:
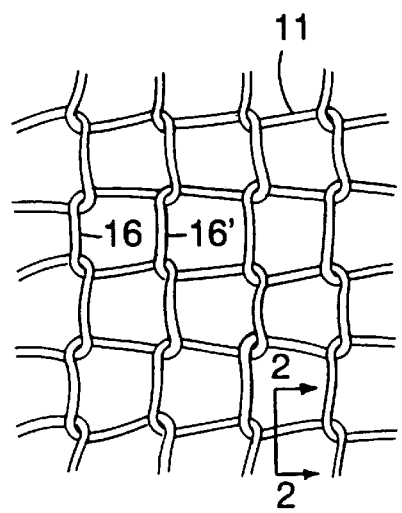
FIG. 1a is an enlarged view of adjacent loops of a filament knitted to form the stent.

Referring to FIGS. 1 and 1a, an endoprosthesis stent 10 according to a preferred embodiment is adapted for use in the biliary tree and formed of an elastic filament 11 knitted into a mesh cylinder 12 that extends to ends 14, 14' coaxially along axis 13 over a working length L, about 4–6 cm and has a maximum expanded diameter, D, of about 9–10 mm. The knitting forms a series of loosely interlocked knitted loops (e.g., as indicated by adjacent loops 16, 16', FIG. 1a) which may slide with respect to each other when the stent is radially compacted, for example, when delivered into the biliary duct on a catheter as further discussed below.

Figure 2:
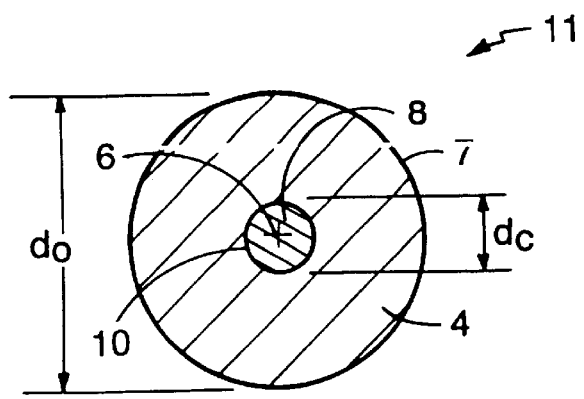
Figure 2A:
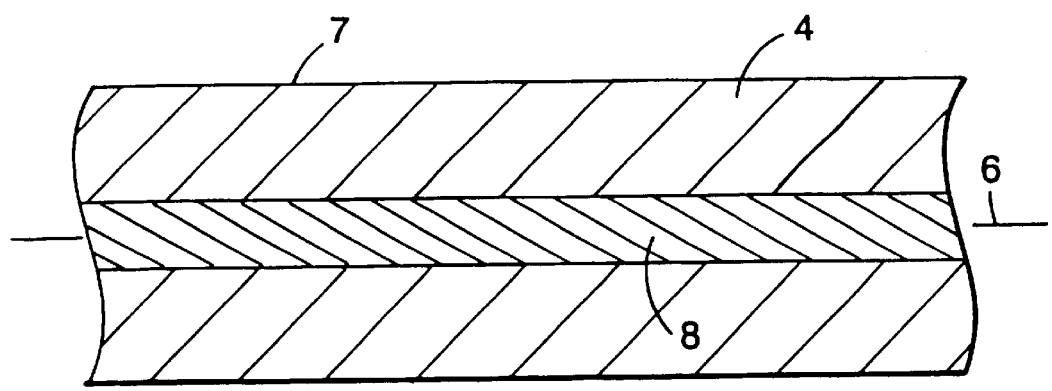
FIG. 2a is a similarly enlarged longitudinal cross-sectional view of a portion of the filament.

Referring to FIGS. 2 and 2a, the filament 11 is a wire-form member that includes a longitudinal outer member 4 concentrically disposed about a central core 8 which extends along an axis 6. The longitudinal member 4, having an outer diameter, $d_o$, about 0.0052 inch, is formed of a metal, such as nitinol, that exhibits desirable properties, such as high elasticity and biocompatibility of its exposed outer surface 7. (The surface 7 may include a non-metal coating of, e.g., fluorocarbons, silicones, hydrophilic and lubricous biocompatible materials.) The core 8 having a diameter, $d_c$, about 0.00175 inch, includes a metal, such as tantalum, with a density greater than the longitudinal member 4 to enhance the radiopacity of the filament and thus the stent from which it is formed. The core 8 is bonded to and substantially enclosed by the outer member 4 such that the core does not have any substantial exposed surface and therefore does not contact body tissue when positioned within the body during use. As illustrated, preferably the core 8 is a continuous solid member in intimate contact with and bonded to the interior portions of the outer member 4 without the formation of substantial voids in the interface 10 between the core and outer member. Preferably, the elastic properties of the filament 11 are dominated by the elastic properties of the longitudinal member 4. The core material 8 enhances the radiopacity of the filament 11 but preferably does not substantially affect the mechanical performance of the filament. One aspect of the present invention is that it has been discovered that a stent can be formed of a composite filament exhibiting substantially the elasticity properties of, for example, a solid elastic (used in linear range) or superelastic nitinol filament, (to form, for example, a self-expanding stent), despite the presence of a dense, e.g. tantalum, core, and that the stent formed of the composite filament is more radiopaque than a stent formed of a solid nitinol filament.

Figure 3:
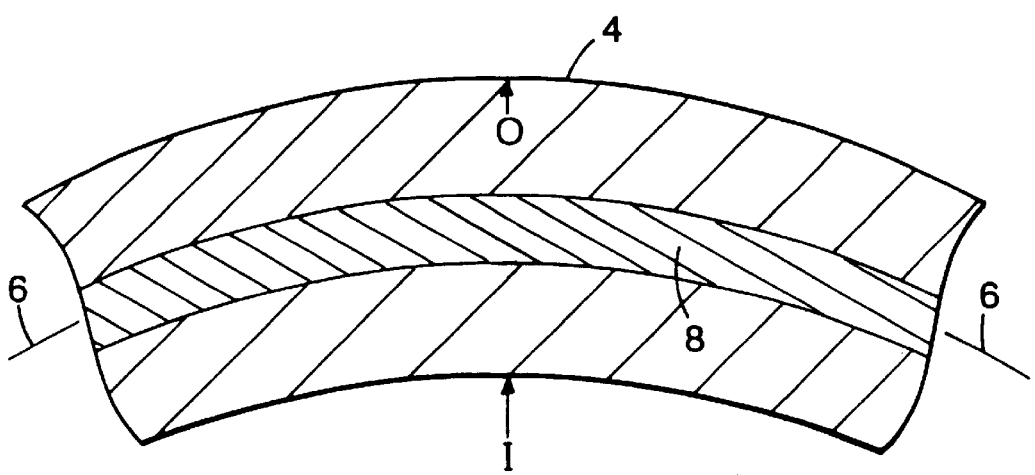
FIG. 3 is a schematic longitudinal cross-sectional view of a stent filament according to FIG. 2 in a bent configuration.

Referring to FIG. 3, the filament 11 is shown in a bent position, as it may be, for example when in use in a knitted stent device. The inner and outer portions (I) and (O), respectively, experience a wide range of compression and tension, as the filament is bent such as during knitting of the stent and during placement of the stent and in use. An advantage of the filament is that by positioning the radiopaque core material 8 near the axis 6, the range of tension and compression imposed on the core is relatively small and a wide latitude of stiff, dense, strong, and/or substantially radiopaque materials can be used which otherwise might not be suitable for their response to bending or other properties.

Parameter Selection

Generally, the characteristics of the filament and thus the selection of the outer member and core metals, is based on the stent application. Particularly preferred uses of stents of the invention are for the biliary tree (e.g. 8–12 mm diameter, 2–8 cm length) such as the hepatic and pancreatic duct (e.g. 4–12 mm diameter), the urinary tract including the prostate and urethra (e.g. 14–15 mm, diameter; 3–4 cm, length) and the ureter (e.g. 3–4 mm diameter), and the vasculature including the hepatic vasculature e.g. for the treatment of portal hypertension (e.g. 4–10 mm diameter; 5–6 cm, length), the neurovasculature (e.g. 1 mm, diameter) and the aorta (e.g. 20 mm, diameter) for example, for treatment of aneurysms or lesions. A filament with a larger outer diameter, $d_o$, may be used for larger stents. For example, a filament outer diameter, $d_o$, in the range of 0.008 inch may be used in the case of an aortic stent.

Typically, the dimension of the core ($d_c$) is less than about 50% (but typically greater than about 1%) of the outer diameter of the filament, more preferably between about 40% and 25%, for example about 33%. Embodiments of the stent having enhanced radiopacity are especially useful in applications where the stent must be sized small with, for example, a stent wire outer diameter ($d_o$) of less than about 0.015 inch, e.g., even less than 0.0075 inch and for which less dense metals are required for advantageous elastic properties. For example, in another embodiment the filament is formed of nitinol with an outer diameter, $d_o$, of about 0.006 inch and a core of tantalum with diameter, $d_c$, at about 0.002 inch.

Figure 4:
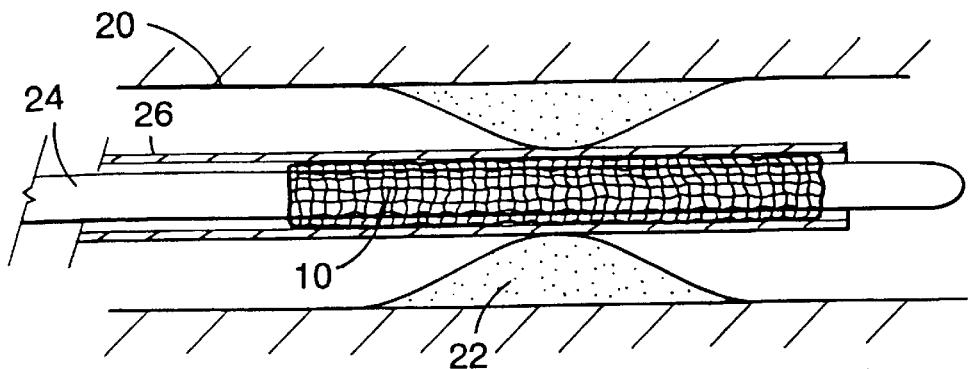
FIGS. 4 to 4b illustrate placement of a self-expanding stent according to the invention.
Figure 4A:
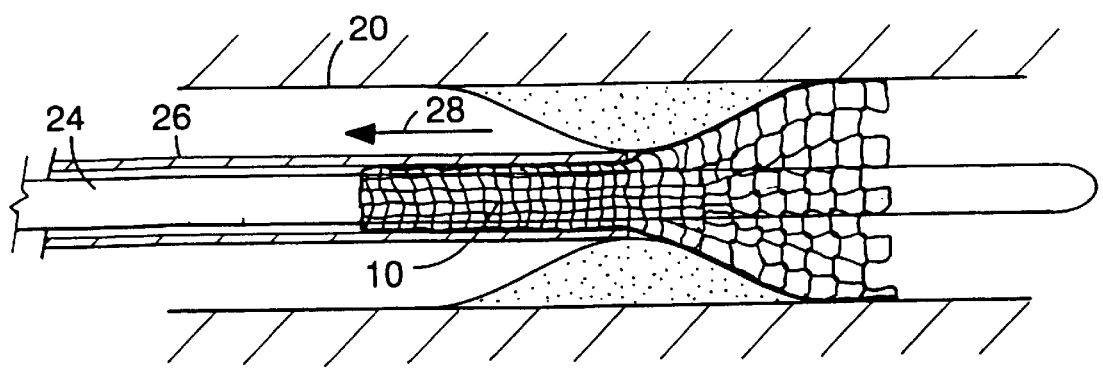
Figure 4B:
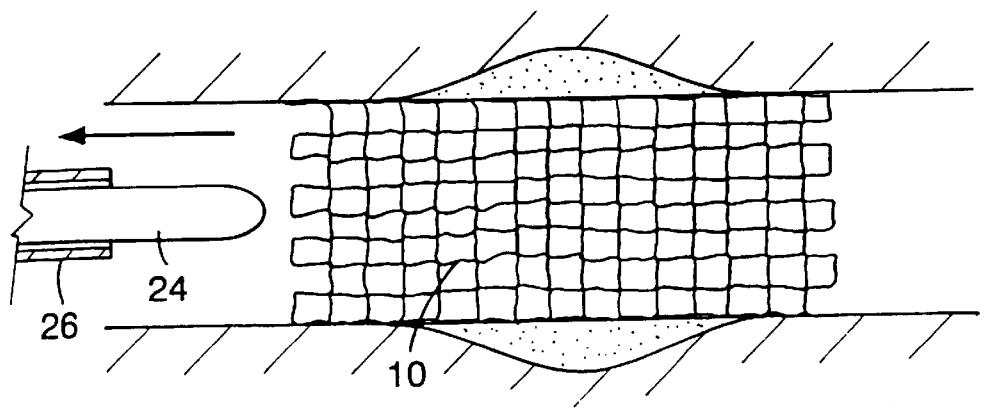

Referring to FIGS. 4 to 4b, in embodiments such as that discussed with respect to FIGS. 1 and 1a, stent 10 is a self-expanding stent that may be introduced to a body lumen 20 such as the biliary tree. The stent 10 is positioned on a catheter 24 which includes a sleeve 26 to maintain the stent 10 in a relatively compact form (FIG. 4). This is typically achieved by rolling the stent upon itself and a pair of tiny mandrels that nip a portion of the wall of the stent and are rotated bodily together until the full circumference of the stent is taken up in the resulting rolled up form. In other cases, the stent may be positioned coaxially over the catheter. The catheter is positioned within the lumen at the region corresponding to a tumor 22 and the sleeve 26 is removed from about the stent 10, for example, by withdrawing axially in the direction of arrow 28, thus causing the stent 10 to radially expand by release of its internal restoring force (FIG. 4a). The internal restoring force is sufficient to dilate the lumen 20 by pushing the tumor growth 22 radially outward (or in some cases compressing the occlusion against the lumen wall), thus opening a passage that allows unobstructed flow through the lumen and allowing removal of the catheter 24 (FIG. 4b). In another embodiment, the stent may be compressed in a tube having a distal axial opening and be pushed from the end of the tube, whereby it self-expands.

Figure 5:
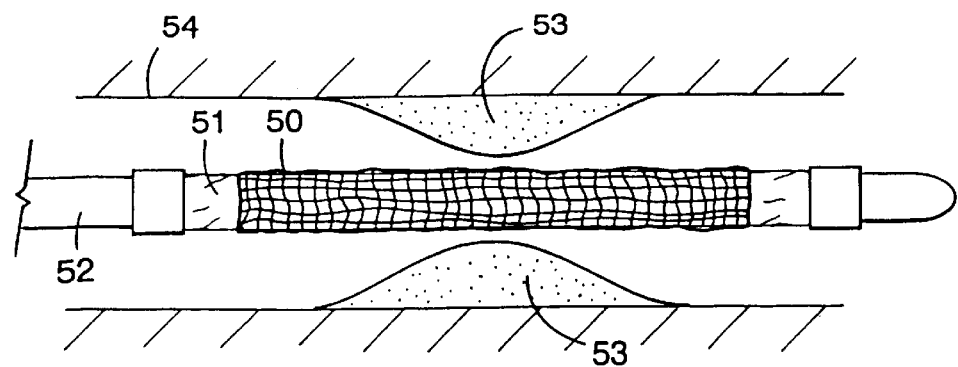
FIGS. 5 to 5b illustrate placement of a plastically deformable stent according to the invention.
Figure 5A:
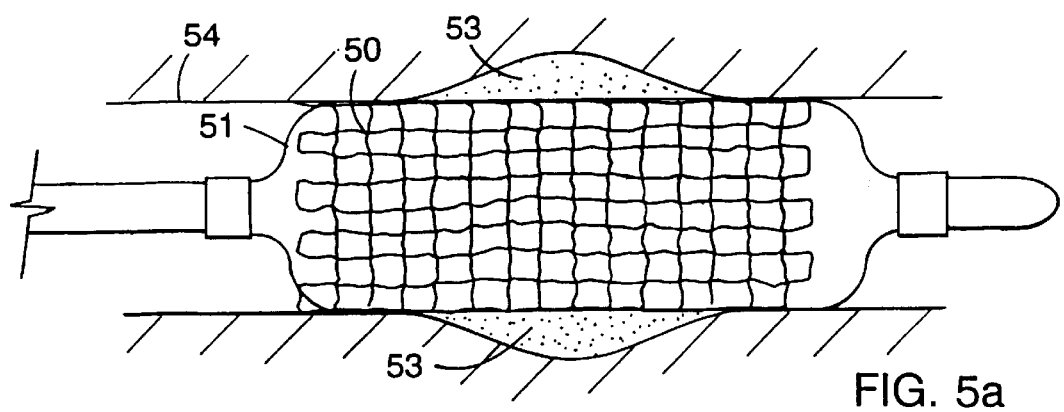
Figure 5B:
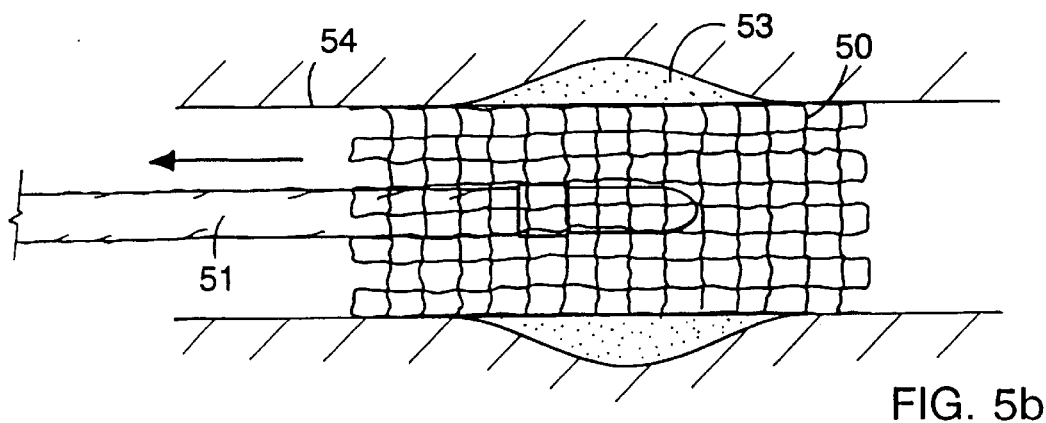

Referring now to FIGS. 5 to 5b, the stent may also be a plastically deformable tube-like knitted structure 50. The individual filament meshes interlock loosely in a looped pattern and during radial expansion of the knitted structure loops forming the individual meshes are deformed beyond the elastic limits of the filament, resulting in plastic deformation of the filament. Stent 50 is placed over a balloon 51 carried near the distal end of a catheter 52. The catheter 52 is directed through a lumen 54, e.g., a blood vessel until the portion carrying the balloon and stent reaches the region of the occlusion 53 (FIG. 5). The stent 50 is then radially expanded beyond its elastic limit by the admission of pressure to the balloon 51 and compressed against the vessel wall with the result that occlusion 53 is compressed, and the vessel wall surrounding it undergoes a radial expansion (FIG. 5a). The pressure is then released from the balloon and the catheter is withdrawn from the vessel (FIG. 5b).

The stent in the balloon expandable embodiment is preferably formed with a dense radiopaque core formed of tantalum and an outer member formed of plastically deformable stainless steel. While the stent filament is plastically deformable, the filament may be selected to have elasticity sufficient to meet the needs of the particular vessel. In addition, self-expanding stents, such as discussed above with respect to FIG. 4 et seq. can be used with a balloon delivery system to aid dilatation of a body lumen.

In various embodiments, the metals used in the filament and their configuration are selected to exhibit various desirable characteristics. For example, the relative dimension of the core and outer member and the particular materials used for these elements may be selected based on the desired over-all mechanical properties of the stent and the degree to which x-ray visibility is to be enhanced, since the core affects the mechanical properties of the filament compared to a solid filament formed of the outer material, and the radiopacity is a function of the sum of the mass between an x-ray beam source and detector. A knitted stent with overlapping portions, may require less radiopaque material to provide sufficient visibility. Similarly, the location of use in the body may affect the amount of dense material needed for sufficient visibility. The visibility of a device can be tested by known techniques such as ASTM Designation F640-79 "Standard Test Method for Radiopacity of Plastics for Medical Use". In this test, the background densities which may be encountered clinically are mimicked by an aluminum plate positioned over the stent having various thicknesses.

The properties of the outer member metal and core which may be considered include density, modulus of elasticity (in annealed and hardened states), biocompatability (primarily a factor for the material of the outer longitudinal member), flexural stiffness, durability, tensile and compression strength, and the required radiopacity and resolution. In some cases, if desirable, the inner and outer metals may be the same metal or metals of the same elemental composition that are different metals because of e.g., different crystal structure or other properties.

In other embodiments of elastic filament members, the outer member is formed of a continuous solid mass of a highly elastic biocompatible metal such as a superelastic or pseudo-elastic metal alloy, for example, a nitinol (e.g., 55% nickel, 45% titanium). Other examples of superelastic materials include, e.g., Silver-Cadmium (Ag—Cd), Gold-Cadmium (Au—Cd), Gold-Copper-Zinc (Au—Cu—Zn), Copper-Aluminum-Nickel (Cu—Al—Ni), Copper-Gold-Zinc (Cu—Au—Zn), Copper-Zinc (Cu—Zn), Copper-Zinc-aluminum (Cu—Zn—Al), Copper-Zinc-Tin (Cu—Zn—Sn), Copper-Zinc-Xenon (Cu—Zn—Xe), Iron Beryllium ($Fe_3Be$), Iron Platinum ($Fe_3Pt$), Indium-Thallium (In—Tl), iron-manganese (Fe—Mn) Nickel-Titanium-Vanadium (Ni—Ti—V), Iron-Nickel-Titanium-Cobalt (Fe—Ni—Ti—Co) and Copper-Tin (Cu—Sn). See Schetsky, L. McDonald, "*Shape Memory Alloys*", *Encyclopedia of Chemical Technology* (3rd ed.), John Wiley & Sons, 1982, vol. 20. pp. 726–736 for a full discussion of superelastic alloys. Preferably in some cases of elastic filament members, nitinol or other highly elastic metal is employed as the outer member, in an arrangement in which it is never stressed beyond the straight line portion of its stress strain curve. Other examples of metals suitable for the outer member include tainless steel or the precursor of superelastic alloys. Precursors of superelastic alloys are those alloys which have the same chemical constituents as superelastic alloys, but have not been processed to impart the superelastic property under the conditions of use. Such alloys are further described in co-owned and co-pending U.S. Ser. No. 07/507,375, filed Apr. 10, 1990, by R. Sahatjian (see also PCT application US91/02420) the entire contents of which is hereby incorporated by reference.

The core material is preferably a continuous solid mass, but may also be in a powder-form. Typically, the core includes a metal that is relatively dense to enhance radiopacity. Preferably, the core metal has a density of about 9.9 g/cc or greater. Most preferably, the core is formed of tantalum (density=16.6 g/cc). Other preferred materials and their density include tungsten (19.3 g/cc), rhenium (21.2 g/cc), bismuth (9.9 g/cc), silver (16.49 g/cc), gold (19.3 g/cc), platinum (21.45 g/cc), and iridium (22.4 g/cc). Typically, the core is somewhat stiffer than the outer member. Preferably, the core metal has a low modulus of elasticity, e.g., preferably below about 550 GPa, e.g., such as tantalum (186 GPa). Generally, a smaller difference between the modulus of elasticity between the outer material and core results in a smaller variation of the modulus from that of the outer material in the filament of the invention. For larger differences, a smaller core may be used so as to produce a filament in which the elastic properties are dominated by the outer material.

The outer member and core may be in many cross-sectional geometric configurations, such as circular, square, triangular, hexagonal, octagonal, trapezoidal and the geometrical configuration of the core may differ from that of the longitudinal member. For example, the outer member of a filament may be rectangular in cross-section with a rectangular core or triangular or hexagonal in cross-section with a circular core. A stent filament may also take on the form of tubing with a lumen within the core extending along the axis. A stent filament may also include successive layers of less dense outer material and more dense core material to form a multi-composite system of three layers or more from exterior to center. The core may extend intermittently along the axis in a desired pattern.

The filament may be a draw-form member formed, for example, by drilling out the center of a relatively large rod of the outer member material to form a bore, positioning a rod of core material in the bore, sealing the ends of the bore, e.g., by crimping, and drawing the form through a series of dies of decreasing diameter until the desired outer diameter is achieved. The component may be heat treated to anneal, harden or impart superelastic properties. Other methods of formation are also possible, e.g., by coating the core with the desired outer material such as by electro- or electroless plating. The materials used in the outer member and core are also selected based on their workability for forming the filament, including factors such as machinability, for forming the longitudinal member into a tubular piece and the core member into a rod shaped piece, stability in gaseous environments at annealing temperatures, properties related to drawing, welding, forging, swaging, the ability to accept coatings such as adhesives, polymers, lubricants and practical aspects such as cost and availability.

As evident from the above, the stents of the invention are preferably constructed by knitting a filament, most preferably on a circular knitting machine. Knitted metal stents are discussed, for example, in Strecker, U.S. Pat. No. 4,922,905. It will be appreciated that the stent may be formed from a composite metal filament by other means such as weaving, crocheting, or forming the filament into a spiral-spring form element. It will further be appreciated that the composite filament may be incorporated within a stent formed from conventional metal or non-metal materials (e.g. dacron in the case of an aortic graft) to contribute desirable properties such as strength and/or radiopacity. The stent may also be in the form of a metal member configured as other than a filament-form, e.g., a composite sheet form member in the form of a cuff or tube.

The following example is illustrative of a stent filament.

EXAMPLE

An elastic, radiopaque filament for use in a stent may be formed as follows. A 500 foot length of filament (0.0052 inch in diameter) having an outer member formed of a precursor of a nitinol (55% Ni/45% Ti) superelastic alloy and a core material of tantalum (0.00175 inch in diameter) is formed by drilling a 0.25 inch diameter bore in a 0.75 inch rod of the outer member material and providing in the drilled lumen a tantalum member of substantially matched outer diameter. The rod is mechanically forged in a standard hot forging and rolling apparatus, then hammered such that no substantial voids between the core and outer longitudinal member are present. One end of the rod is sealed and the opposite end is cold drawn longitudinally through a die to the final diameter. Initially, the outer member of the filament is the precursor of a superelastic alloy, i.e., it has not been heat treated to impart the superelastic property under the anticipated conditions of use.

Figure 6:
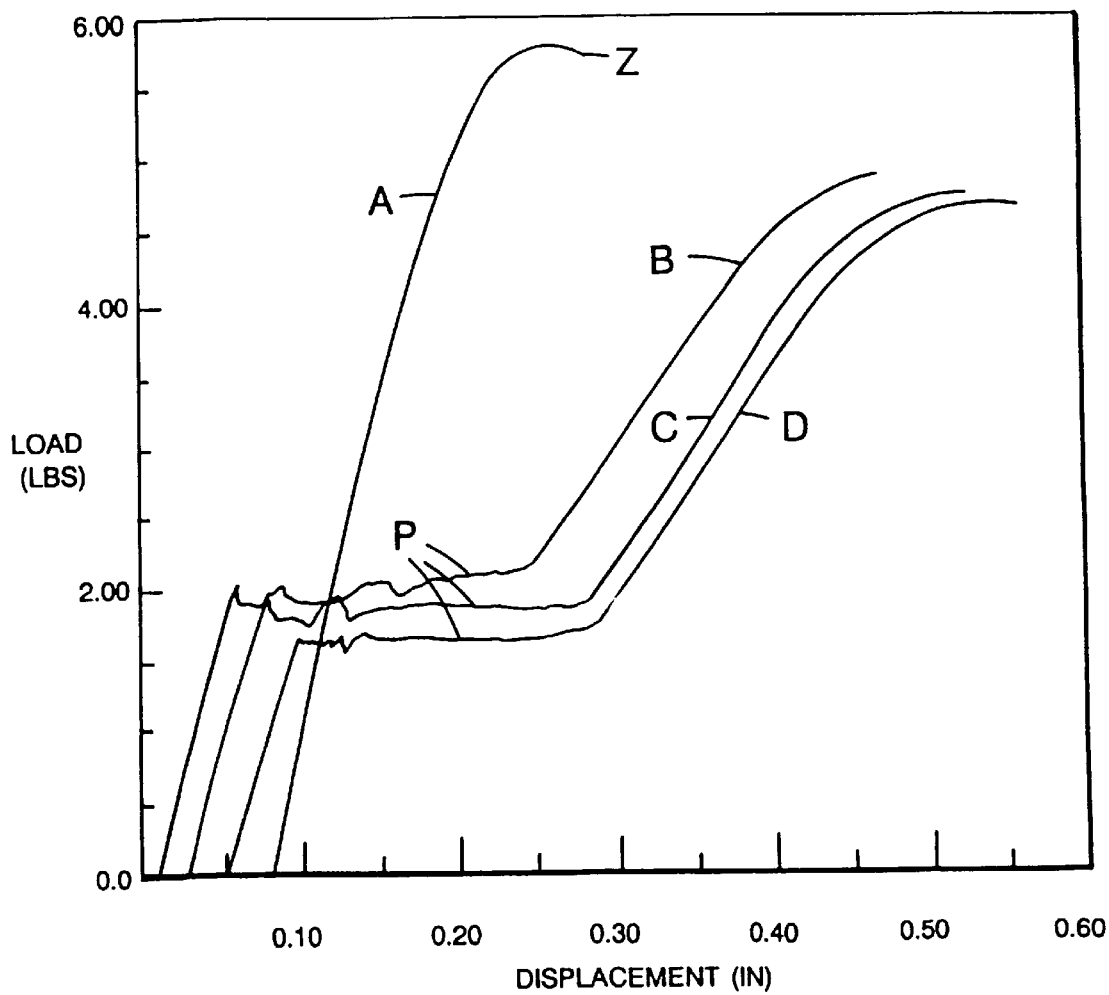
FIG. 6 is a graph of load as a function of displacement for several stent wires according to the invention.

Referring to FIG. 6, load versus displacement curves are illustrated. (For clarity, curves C, D and A are offset, successively, 0.025 inch on the x-axis.) Curve A illustrates the filament as discussed in the above paragraph prior to heat annealing which induces the superelastic property; the filament exhibits substantially linear elastic strain as a function of stress to a break point z. Curves B, C, D illustrate stress/strain curves after annealing the filament at 460° C. for 3 minutes, 5 minutes and 15 minutes, respectively. As these curves illustrate, the superelastic nature of the filament is substantially preserved, as evidenced by the substantial plateaus (p) on the stress/strain curve, despite the presence of the tantalum core. Also as illustrated, the stress at which constant displacement occurs decreases with increasing annealing, as would be expected with a superelastic material. The mechanical properties of the filament, therefore, are dominated by the nitinol alloy, despite the presence of the tantalum core.

Referring to Table I, the modulus of elasticity and plateau stress calculated based on stress-strain measurements as above, are compared for the filaments of the invention and a solid filament of Ni—Ti alloy.

prised of a core of a first metal of a first selected thickness and an intimately surrounding sheath of a second selected metal of a second thickness, said first metal being of a substantially higher radiopacity than that of said second metal, said second metal being substantially more elastic than said first metal, the metals in said filament-form metal element serving to enhance the radiopacity of said filament-form metal element to provide improved fluoroscopic or x-ray visualization of said filament-form metal element in said body while imparting sufficient elasticity to enable the

TABLE I

|  | Ni—Ti | Ta Cored Ni—Ti | % Charge in Cored Filament |
|---|---|---|---|
| Diameter | .0038" | .0052" | — |
| Area | $1.134 \times 10^{-5}$ in$^2$ | $2.124 \times 10^{-5}$ in$^2$ | — |
| (Modulus of Elasticity) | | | |
| Precursor | 5,401,300 psi | 7,373,865 psi | +27% |
| 460° @ 3 mins | 6,967,150 psi | 6,657,000 psi | −4.5% |
| 460° @ 5 mins | 5,381,160 psi | 5,721,100 psi | +6.0% |
| 460° @ 10 mins | 5,139,310 psi | — | — |
| 460° @ 15 mins | 5,143,960 psi | 5,551,924 | +7.4% |
| Plateau Stress | | | |
| (loading) | | | |
| 460° @ 3 mins | 101,400 psi | 94,174 | −7.2% |
| 460° @ 5 mins | 89,056 psi | 84,757 | −4.8% |
| 460° @ 10 mins | 79,357 psi | — | — |
| 460° @ 15 mins | 72,303 psi | 75,339 psi | +4.1% |

As the results in Table I illustrate, the modulus of elasticity of the filaments of the invention was varied less than 30% compared to the solid Ni—Ti filament. The plateau stress of the filaments of the invention using a superelastic outer member was varied less than about 10% compared to a solid Ni—Ti superelastic filament. The composite filament formed as described exhibits about 30% or more enhanced x-ray visibility over a filament of the same thickness formed of solid nitinol.

It will be understood that such filaments may be employed both in instances where the superelastic property is employed, and in instances where it is not (all stress within the straight line portion of the stress strain curve).

The visibility of a knitted stent formed from the filament was greater than a comparison stent using a solid nitinol filament of larger (0.006 inch) diameter, yet using the stent of the invention, the force needed for radial compression of the stent was reduced compared to the stent formed of the thicker nitinol filament. Thus, radiopacity of the stent was enhanced while mechanical properties were dominated by the outer member, nitinol. Placement of the stent, as described above, can be monitored by x-ray fluoroscopy.

Preferably, filaments as described, dominated by the mechanical properties of an outer member, such as nitinol, and exhibiting generally satisfactory radiopacity have outer diameter ($d_o$) of about 0.008 to 0.0045 inch with a core, for example of tantalum, with diameter ($d_c$) of about 0.0014 to 0.00195 inch.

Other embodiments are in the following claims.

What is claimed is:

1. A tubular prosthesis device for use within the body comprised at least in part of an elongated filament-form metal element adapted to be subjected to elastic deformation to enable the device to be forced into a characteristic deformed configuration during a stage of use and to elastically self-recover from said deformation when deformation forces are relieved, said filament-form metal element com- filament-form metal element to elastically self-recover from said characteristic deformed configuration.

2. The device of claim 1, wherein said filament-form metal element is the product produced by draw-forming.

3. The device of claim 1, wherein said second metal is nitinol.

4. The device of claim 3, wherein said high density metal is tantalum.

5. The device of claim 1, wherein said tubular prosthetic device is formed into said tubular shape by knitting into loosely interlocked loops of said filament-form metal element.

6. The device of claim 1, wherein the transverse cross-sectional dimension of said filament-form metal element is about no greater than 0.015 inch.

7. The device of claim 1, wherein said transverse cross-sectional dimension of said filament-form metal is about 0.0045 to about 0.006 inch and said core has a transverse cross-sectional dimension of about 0.0014 to about 0.00195 inch.

8. The device of claim 1, wherein said core has a density of about at least 9.9 g/cc.

9. The device of claim 8, wherein said core is selected from the group consisting of tungsten, tantalum, rhenium, iridium, silver, gold, bismuth and platinum.

10. The device of claim 1, wherein said outer member is selected from superelastic alloys and precursors of superelastic alloys.

11. The device of claim 10, wherein said outer member is nitinol.

12. The device of claim 11, wherein said core is tantalum.

13. The device of claim 1, wherein a transverse cross-sectional dimension of said core is about 1 to 40% of a transverse cross-sectional dimension of said filament-form metal element.

14. The device of claim 13, wherein said core is about 25 to 40% of a transverse cross-sectional dimension of said filament-form metal element.

15. The device of claim 13, wherein said core is about 33% of a transverse cross-sectional dimension of said filament-form metal element.

16. The device of claim 1, wherein said core has a modulus of elasticity of about no greater than 500 GPa.

17. The device of claim 1, wherein said core has a modulus of elasticity of about no greater than 200 GPa.

18. The device of claim 1, wherein said filament-form metal element has a transverse cross-sectional dimension of less than about 0.0075 inch.

19. The device of claim 1, wherein said filament-form metal element has a transverse cross-sectional dimension of about 0.0045 inch to about 0.006 inch.

20. The device of claim 1, wherein said stent device has a diameter of about 4 mm to about 12 mm.

21. The device of claim 1, wherein said stent device has a length of about 2 cm to about 8 cm.

22. The device of claim 1, wherein said filament-form metal element is in an overlapping pattern.

23. The device of claim 1, wherein said stent device is a weave of said filament-form metal element.

24. The device of claim 1 or 18–23, wherein said first metal is tantalum.

25. A tubular prosthesis for use within the body comprised at least in part of an elongated filament-form metal element, said filament-form metal element being arranged in an overlapping pattern defining a tube and adapted to be subjected to elastic deformation to enable the device to be forced into a characteristic deformed configuration during a stage of use and to elastically self-recover from said deformation when deformation forces are relieved, said filament-form metal element having transverse cross-sectional dimension of about 0.0075 inch or less and being comprised of a core of a first metal of a first selected thickness and an intimately surrounding sheath of a second selected metal of a second thickness, said first metal being tantalum and having a substantially higher density and demonstrating characteristically substantially higher radiopacity than that of said second metal, said second metal being substantially more elastic than said first metal, the combined effect of said first and second metals in said filament-form metal element to provide improved fluoroscopic or x-ray visualization of said filament-form metal element in said body while imparting sufficient elasticity to enable the filament-form metal element to elastically self-recover from said characteristic deformed configuration.

26. An implantable tubular medical stent, comprising:
a metal wire composed of multiple metal layers, including a first layer formed of a first metal and a second layer formed of a second metal, the first metal having a greater density than the second metal and the first layer being disposed inwardly of the second layer.

27. The implantable tubular stent of claim 26, wherein the wire is formed by draw-forming.

28. The implantable tubular stent of claim 26, wherein the second metal is nitinol.

29. The implantable tubular stent of claim 28, wherein the first metal is tantalum.

30. The implantable tubular stent of claim 26, wherein the stent is formed by knitting, weaving or crocheting the wire.

31. The implantable tubular stent of claim 26, wherein the wire has an overall diameter of no greater than about 0.015 inch.

32. The implantable tubular stent of claim 26, wherein the first metal has a density of at least about 9.9 g/cc.

33. The implantable tubular stent of claim 26, wherein the first metal is selected from the group consisting of stainless steel, tantalum, rhenium, iridium, silver, gold, bismuth and platinum.

34. The implantable tubular stent of claim 26, wherein the second metal is selected from the group consisting of stainless steel, superelastic alloys and precursors of superelastic alloys.

35. The implantable tubular stent of claim 26, wherein the second metal is nitinol.

36. The implantable tubular stent of claim 35, wherein the first metal is tantalum.

37. The implantable tubular stent of claim 26, wherein the core has a diameter of about 1 to 40% of an overall diameter of the wire.

38. The implantable tubular stent of claim 37, wherein the wire has an overall diameter of about 0.0045 to 0.006 inch and the core has a diameter of about 0.0014 to 0.00195 inch.

39. The implantable tubular stent of claim 37, wherein the core has a diameter of about 25% to 40% of the overall diameter of the wire.

40. The implantable tubular stent of claim 39, wherein the core is about 33% of the overall diameter of the wire.

41. The implantable tubular stent of claim 26, wherein the first metal has a modulus of elasticity of no greater than about 500 GPa.

42. The implantable tubular stent of claim 41, wherein the first metal has a modulus of elasticity of no greater than about 200 GPa.

43. The implantable tubular stent of claim 26, wherein the stent has a length in the range of about 2–8 cm.

44. The implantable tubular stent of claim 43, wherein the stent has a diameter in the range of about 4–12 mm.

45. An implantable tubular medical stent, comprising:
a metal wire composed of multiple metal layers, including a first layer formed of a first metal and a second layer formed of a second metal, the first metal having a greater density than the second metal and being selected from the group consisting of tantalum, platinum, tungsten and iridium, the first layer being disposed inwardly of the second layer.

46. The implantable tubular stent of claim 45, wherein the first metal is tantalum.

47. The implantable tubular stent of claim 45, wherein the core has a diameter greater than about 1% of an overall diameter of the wire.

48. The implantable tubular stent of claim 47, wherein the core has a diameter of about 50% or less of the overall diameter of the wire.

49. The implantable tubular stent of claim 45, wherein the second metal is selected from the group consisting of stainless steel, superelastic alloys and precursors of superelastic alloys.

50. The implantable tubular stent of claim 45, wherein the stent has a length of about 2–8 cm and a diameter in the range of about 4–12 mm.

51. The implantable tubular stent of claim 45, where in the wire has a diameter of about 0.0075 inch or less.

52. The implantable tubular stent of claim 46, where in the wire has a diameter of about 0.0075 inch or less.

53. The implantable tubular stent of claim 47, where in the wire has a diameter of about 0.0075 inch or less.

54. The implantable tubular stent of claim 48, where in the wire has a diameter of about 0.0075 inch or less.

55. The implantable tubular stent of claim 49, where in the wire has a diameter of about 0.0075 inch or less.

* * * * *